US006613516B1

(12) United States Patent
Christians et al.

(10) Patent No.: US 6,613,516 B1
(45) Date of Patent: Sep. 2, 2003

(54) PREPARATION OF NUCLEIC ACID SAMPLES

(75) Inventors: Fred C. Christians, Los Altos, CA (US); Duc Do, San Jose, CA (US); Thomas Gingeras, Encinitas, CA (US); Kevin Gunderson, Encinitas, CA (US); Charles G. Miyada, San Jose, CA (US); Carsten Rosenow, Redwood City, CA (US); Kai Wu, Mountain View, CA (US); Qing Yang, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 255 days.

(21) Appl. No.: 09/689,937

(22) Filed: Oct. 11, 2000

Related U.S. Application Data

(60) Provisional application No. 60/191,345, filed on Mar. 22, 2000, and provisional application No. 60/162,739, filed on Oct. 30, 1999.

(51) Int. Cl.$^7$ .......................... C12Q 1/68; G01N 33/53; G01N 33/566; C07H 21/04; C07H 21/02
(52) U.S. Cl. .......................... 435/6; 435/7.1; 435/91.1; 435/91.2; 435/91.32; 435/194; 435/196; 435/288.3; 436/501; 536/23.1; 536/24.33; 536/25.3
(58) Field of Search ...................... 435/6, 287.1, 287.9, 435/2.1, 91.1, 196, 7.5, 7.72, 7.9, 7.92, 15, 18, 252.33, 849; 536/25.3, 25.4

(56) References Cited

U.S. PATENT DOCUMENTS

| | | | |
|---|---|---|---|
| 4,672,040 A | 6/1987 | Josephson | |
| 4,711,955 A | 12/1987 | Ward et al. | |
| 4,943,523 A | 7/1990 | Stavrianopoulos | |
| 4,952,685 A | 8/1990 | Stavrianopoulos | |
| 4,994,373 A | 2/1991 | Stavrianopoulos | |
| 5,002,885 A | 3/1991 | Stavrianopoulos | |
| 5,013,831 A | 5/1991 | Stavrianopoulos | |
| 5,082,830 A | 1/1992 | Brakel et al. | |
| 5,175,269 A | 12/1992 | Stavrianopoulos | |
| 5,241,060 A | 8/1993 | Engelhardt et al. | |
| 5,328,824 A | 7/1994 | Ward et al. | |
| 5,447,848 A | 9/1995 | Barns et al. | |
| 5,449,767 A | 9/1995 | Ward et al. | |
| 5,567,587 A | 10/1996 | Kohne | |
| 5,643,761 A | 7/1997 | Fisher et al. | |
| 5,665,549 A | 9/1997 | Pinkel et al. | |
| 5,723,597 A | 3/1998 | Kohne | |
| 5,759,778 A * | 6/1998 | Li et al. ......................... | 435/6 |
| 5,759,820 A | 6/1998 | Hornes et al. | |
| 5,804,382 A | 9/1998 | Sytkowski et al. | |
| 5,807,718 A * | 9/1998 | Joyce et al. ............... | 435/91.5 |
| 5,830,645 A | 11/1998 | Pinkel et al. | |
| 5,851,805 A | 12/1998 | Wei et al. | |
| 2001/0049094 A1 * | 12/2001 | Alland et al. .................. | 435/6 |

FOREIGN PATENT DOCUMENTS

| | | |
|---|---|---|
| CA | 1219824 | 3/1987 |
| CA | 1223831 | 7/1987 |
| CA | 1228811 | 11/1987 |
| CA | 1254525 | 5/1989 |
| CA | 1309672 | 11/1992 |
| EP | 0 063 879 B1 | 11/1989 |
| EP | 0 117 440 B1 | 4/1993 |
| EP | 0 122 614 B1 | 7/1993 |
| EP | 0 128 332 B1 | 8/1995 |

OTHER PUBLICATIONS

Sang Jeong and Theo Nikiforov "Kinase Assay Based on Thiophosphorylation and Biotinylation" Biotechniques 27:1232–1238 (Dec. 1999).

* cited by examiner

*Primary Examiner*—Stephanie Zitomer
(74) *Attorney, Agent, or Firm*—Sandra Wells; Philip L. McGarrigel

(57) ABSTRACT

The presently claimed invention provides methods, compositions, and apparatus for studying nucleic acids. Specifically, the present invention provides a novel enrichment and labeling strategy for ribonucleic acids. In one embodiment, the invention provides enriching for a population of interest in a complex population by diminishing the presence of a target sequence. In a further embodiment, the invention can be used to reproducibly label and detect extremely small amounts of nucleic acids.

41 Claims, 16 Drawing Sheets

1 = 1 ug total RNA, untreated

2 = 1 ug total RNA + enrichment
    − RNase H

3 = 1 ug total RNA + enrichment
    + RNase H

A  B

PREPARATION OF NUCLEIC ACID SAMPLES

RELATED APPLICATIONS

This application claims the benefit of U.S. Provisional Application No. 60/162,739, filed Oct. 30, 1999, and U.S. Provisional Application No. 60/191,345, filed Mar. 22, 2000, both of which are fully incorporated herein by reference for all purposes.

BACKGROUND OF THE INVENTION

Novel methods for enriching and labeling nucleic acids are needed. For example, gene expression analysis techniques often employ isolation and labeling of ribonucleic acid (RNA). Because of the interest in identifying protein-encoding genes and in examining gene expression levels, it is often desirable to purify or enrich the messenger RNA (mRNA). The poly-adenine 3'-terminus (poly-A tail) of mRNA from eukaryotic cells can be used as a handle to bind to poly(dT) oligonucleotides, and this method is widely used to identify, purify and or label eukaryotic mRNA. However, because prokaryotic mRNA generally lacks poly-A tails, there is a need for alternative methods for purifying and labeling mRNA samples which do not rely on the existence of a poly-A tail.

SUMMARY OF THE INVENTION

The presently claimed invention provides methods of preparing a nucleic acid sample for analysis.

In a first embodiment, the presently claimed invention provides a method of preparing a nucleic acid sample for analysis comprising enriching for a population of interest within a mixed population of nucleic acids by contacting the nucleic acid sample with a bait molecule. The bait molecule is capable of complexing specifically to unwanted target sequences within the nucleic acid sample, but is incapable of complexing with sequences from the population of interest. The bait molecule is contacted with the target sequences forming bait:target complexes which are then specifically removed from the nucleic acid sample. The remaining enriched population of interest is then fragmented and a signal moiety is attached to the fragments.

In a second embodiment, the presently claimed invention provides a method of enriching for a population of interest within a mixed population of nucleic acids by contacting the nucleic acid with a bait molecule. The bait molecule is capable of complexing specifically to unwanted target sequences within the nucleic acid sample, but is incapable of complexing with sequences from the population of interest. The bait molecule is contacted with the target sequences forming bait:target complexes which are then specifically removed from the nucleic acid sample. Thus enriching for the population of interest.

In a third embodiment, the presently claimed invention provides a compound having the formula:

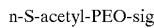

where n is a polynucleotide, S is a thiol group, acetyl is an acetyl functional group, PEO is polyethelene oxide, and sig is a signal moiety.

In a fourth embodiment, the presently claimed invention provides a method for labeling a polynucleotide comprising contacting the polynucleotide with a PEO-iodoacetyl conjugated to a signal moiety under conditions such that the PEO-iodoacetyl will attach to said nucleotide.

In a fifth embodiment, the presently claimed invention provides a method for labeling a polynucleotide comprising: contacting the polynucleotide with a reactive thiol group to form a thiolated polynucleotide and contacting the thiolated polynucleotide with either a signal moiety capable of reacting with said thiolated polynucleotide under appropriate conditions such that said signal moiety is attached to said polynucleotide.

In a sixth embodiment, the presently claimed invention provides a method for labeling prokaryotic mRNA comprising: obtaining a population of RNA from a prokaryotic organism; enriching the population for mRNA by exposing the population to a plurality of DNA bait molecules which are complementary to at least a portion of the stable RNA in said population under such conditions as to allow for the formation of DNA:RNA hybrids; exposing the DNA:RNA hybrids to RNAse H to remove the RNA from said DNA:RNA hybrids; exposing the remaining DNA to DNase I to remove the DNA, thus producing an enriched population of mRNA; fragmenting the enriched mRNA to form mRNA fragments; exposing the mRNA fragments to (-S-ATP and T4 kinase to produce reactive thiol groups at the 5' ends of the mRNA fragments; and exposing the thiolated mRNA fragments to PEO-Iodoacetyl-Biotin such that a stable thio-ether bond is formed between said thiolated mRNA fragments and said PEO-Iodoacetyl-Biotin.

DETAILED DESCRIPTION OF THE PREFERRED EMBODIMENTS

1. Definitions

Figure 1:
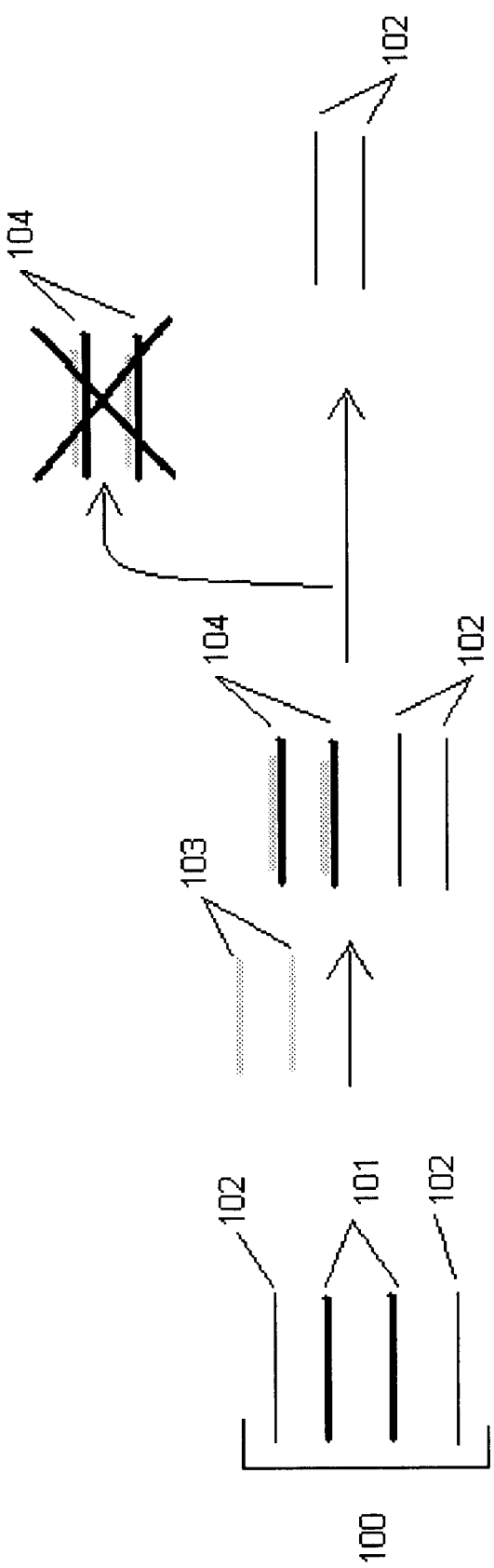
FIG. 1 depicts a schematic illustration of one embodiment of the presently claimed invention in which target sequences are depleted from a mixed population of nucleic acids.

The phrase "massively parallel screening" refers to the simultaneous screening of at least about 100, preferably about 1000, more preferably about 10,000 and most preferably about 1,000,000 different nucleic acid hybridizations.

The terms "nucleic acid" or "nucleic acid molecule" refer to a deoxyribonucleotide or ribonucleotide polymer in either single-or double-stranded form, and unless otherwise limited, would encompass analogs and mimetics of natural nucleotides that can function in a similar manner as naturally occurring nucleotides. Nucleic acids may be derived from a variety of sources including, but not limited to, natural or naturally occurring nucleic acids or mimetics thereof, clones, synthesis in solution or solid phase synthesis.

An "oligonucleotide" or "polynucleotide" is a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

"Subsequence" refers to a sequence of nucleic acids that comprise a part of a longer sequence of nucleic acids.

The phrase "hybridizing specifically to" refers to the binding, duplexing, or hybridizing of a molecule substantially to or only to a particular nucleotide sequence or sequences under stringent conditions when that sequence is present in a complex mixture (e.g., total cellular) DNA or RNA. Standard conditions are described in, for example, Sambrook, Fritsch, Maniatis "Molecular Cloning: A Laboratory Manual" (1989) Cold Spring Harbor Press.

The term "mRNA" or "mRNA transcripts," as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "signal moiety" refers in a general sense to a detectable moiety, such as a radioactive isotope or group containing the same, and non-isotopic moieties, such as enzymes, biotin, avidin, streptavidin, digoxygenin, luminescent agents, dyes, haptens and the like. Luminescent agents, depending upon the source exciting the energy, can be classified as radioluminescent, chemiluminescent, bioluminescent, and photoluminescent (fluorescent).

The phrase "mixed population" or "complex population" refers to any sample containing both desired and undesired nucleic acids. As a non-limiting example, a complex population of nucleic acids may be total genomic DNA, total cellular RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

Throughout the disclosure various Patents, Patent Applications and publications are referenced. Unless otherwise indicated, each is incorporated by reference in its entirety for all purposes.

2. General

In a first embodiment, the presently claimed invention provides a method of preparing a nucleic acid sample for analysis. It is often desirable to isolate, enrich, or increase the relative percentage of a particular population of sequences within a much larger population of sequences in order to limit analysis to those sequences of interest and to reduce interference and unnecessary work which may be caused by the presence of undesirable sequences. The methods of the presently claimed invention provide a novel method wherein a complex sample is depleted of undesired sequences and is thus enriched for a population of interest. One particularly preferred enrichment is to increase the relative percentage of prokaryotic mRNA in a given sample for further analysis.

Briefly, the method enriches for a population of interest within a mixed population of nucleic acid sequences by targeting undesired sequences (target sequences) and removing them from the mixed population. First, a mixed population of nucleic acid sequences is exposed to a bait molecule. The bait molecule is capable of complexing specifically to a target sequence but not to the sequences in the population of interest. The bait molecule is allowed to form a complex with the target sequence and this complex is then specifically recognized and removed. The removal process may be conducted in a single step, or may involve removing first the target sequences and then the subsequent removal of the bait molecule. In one particular example the bait molecules are short DNA sequences which are complementary to the target sequences.

FIG. 1 illustrates a general embodiment of the presently claimed invention. A mixed population 100 comprising a population of interest 102 and target sequences 101 is exposed to bait molecules 103. The bait molecules complex with the target sequences to form bait:target complexes 104. The bait:target complex is then removed from the mixed population thereby enriching for the population of interest.

The mixed population of nucleic acids may be any nucleic acid sample comprising both desired and undesired sequences. The population may include different DNA or RNA molecules. In a preferred embodiment, the mixed population is an RNA sample, in a further preferred embodiment the nucleic acid sample is RNA derived from a prokaryotic organism. The mixed population may be derived from a wide variety of sources including for example, tissue samples, blood, isolated cells or environmental samples such as water or soil. The mixed population may be derived from any organism including both eukaryotes and prokaryotes such as human, rat, mouse, *Escherichia coli* (*E. coli*), *Bacillus subtilis* (*B. subtilis*), *Pseudomonas aerugionosa*, etc. Methods of deriving nucleic acid samples from eukaryotic and prokaryotic organisms will be well known to those of skill in the art. See for example, Chapter 4, "Current Protocols in Molecular Biology," Ausubel et al., eds (1997 supplement) Johan Wilen & Sons, Inc. and Chapter 7, Sambrook, Fritsch, Maniatis "Molecular Cloning: A Laboratory Manual" (1989) Cold Spring Harbor Press, etc.

The population of interest may be any subset of the mixed population. The population of interest may include RNA and/or DNA. The population of interest may, for example, be a particular type of RNA. In a preferred embodiment the population of interest is mRNA. The population of interest may comprise any sequence and the sequence need not be known. The population of interest may be chosen on any basis, including by sequence, function (i.e. messenger RNA (mRNA), ribosomal RNA (rRNA), transfer RNA (tRNA), etc.) or a combination thereof The target sequences may be any undesired sequences in the mixed population. The target sequences may comprise any sequence so long as they are distinguishable by sequence from the population of interest. Target sequences may be chosen on any basis, including by sequence, function (i.e. mRNA, rRNA, tRNA, etc.) or a combination thereof. In a preferred embodiment the target sequences are stable RNAs including rRNA and tRNA. In some embodiments, it may not be necessary to remove all the undesired sequences from the mixed population. In these embodiments it is acceptable to remove only enough of the undesired sequences such that the undesired sequences do not interfere with analysis of the population of interest. For example, in a prokaryotic expression study utilizing array hybridization techniques, it may be desirable to remove rRNA sequences which may interfere with hybridization of the mRNAs to the array by creating a significant background signal. In this example, it may be acceptable to remove only the 23S and 16S RNAs, as removing these sequences reduces background signals to acceptable levels. See, e.g. example 1, below.

In a preferred embodiment any non-targeted undesirable sequences represent only a small proportion of the mixed population. These non-targeted undesirable sequences may include a variety of other nucleic acids such as DNAs, rRNAs, mRNAs or tRNAs. For the sake of simplicity, the presence of non-targeted RNAs will not be discussed throughout the remainder of the application, however, the possibility of their presence is contemplated by the scope of the presently claimed invention.

The bait molecules may be obtained and added in a variety of methods. The bait molecules should be able to recognize and complex specifically with the target molecule, but should not complex with the sequences from the population of interest. Moreover, the bait:target complex should have a particular property which makes is vulnerable to a selection and removal mechanism.

Figure 2:
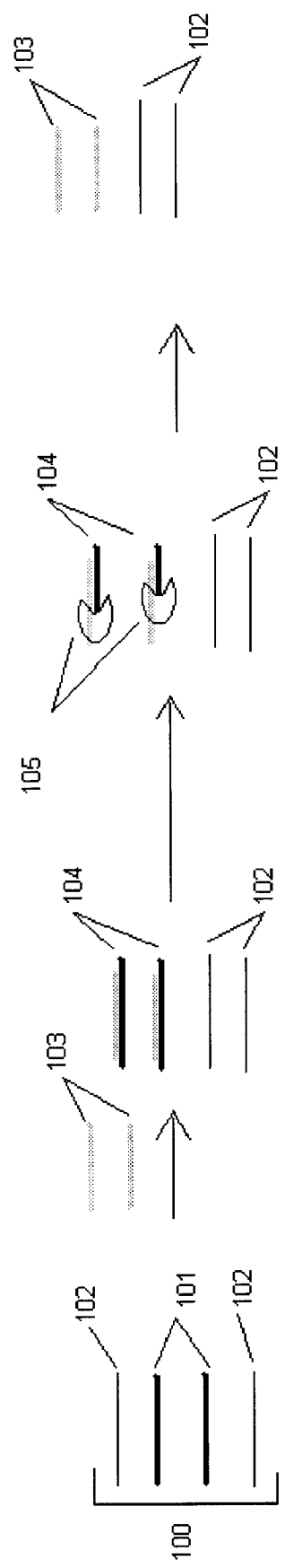
FIG. 2 depicts a schematic illustration of one embodiment of the presently claimed invention wherein target sequences are complexed to a bait molecule and then specifically digested.

In one embodiment, the bait:target complex is targeted by an enzyme or process which specifically removes any target sequences which are complexed to a bait molecule. FIG. 2 depicts a schematic illustration of this embodiment. A mixed population 100 comprises a population of interest 102 and target sequences 101. Bait molecules 103 are introduced to complex specifically with the target sequences forming bait:target complex 104. An enzyme or process 105 is introduced to specifically remove the target sequences from the bait:target complexes without interfering with the sequences from the population of interest. After removal of the target sequences, the mixed population is comprised of the population of interest and the bait molecules. If desired, the bait molecules may then be removed. (Step not shown.)

As one example, the bait sequence may be DNA and the target sequence may be RNA. In this example the bait:target complex would be a DNA:RNA hybrid. The DNA:RNA hybrid is then removed from the mixed population. For example, in some embodiments an enzyme which specifically targets DNA:RNA hybrids will be used to remove the DNA:RNA hybrid. In a preferred embodiment, RNAse H is used to specifically hydrolyze RNA which is part of a DNA:RNA hybrid. The remaining DNA is then available to hybridize with another RNA target sequence. If desired, the DNA may then be removed by addition of enzymes which specifically target and digest DNA. In a preferred embodiment DNAse I is used. Alternatively, physical or other methods of removal may likewise be employed such as straptavidin to remove biotinylated DNA.

A particular example of the presently claimed invention provides a method of isolating or enriching for mRNAs within a mixed population of RNAs by specifically removing targeted rRNAs. A mixed population of RNAs includes mRNAs, tRNAs and rRNAs. DNA bait molecules which are complementary to the rRNAs but not to the mRNAs are added to the mixed population under conditions suitable to allow for the formation of DNA:RNA hybrids. Then, RNAse H specifically targets and removes any RNA which is part of a DNA:RNA hybrid, yielding DNA bait molecules and an enriched population of mRNAs.

If a DNA bait sequence is used, the DNA may be generated exogenously, chemically obtained, or synthesized from another biological source. Exogenous DNA may be generated by chemical or non-biological synthesis. Alternatively, exogenous DNA may be obtained through biological synthesis, for example, through the production by bacteria of double stranded plasmid DNA or single stranded phage DNA containing the bait sequence. Chemical or non-biological methods of synthesizing DNA will be known to those of skill in the art and are described in, for example, Innis et al. (eds.) (1990) PCR Protocols: A Guide to Methods and Applications, Academic Press; and Gait (1984) Oligonucleotide Synthesis: A Practical Approach, IRL Press, Oxford.

Figure 3:
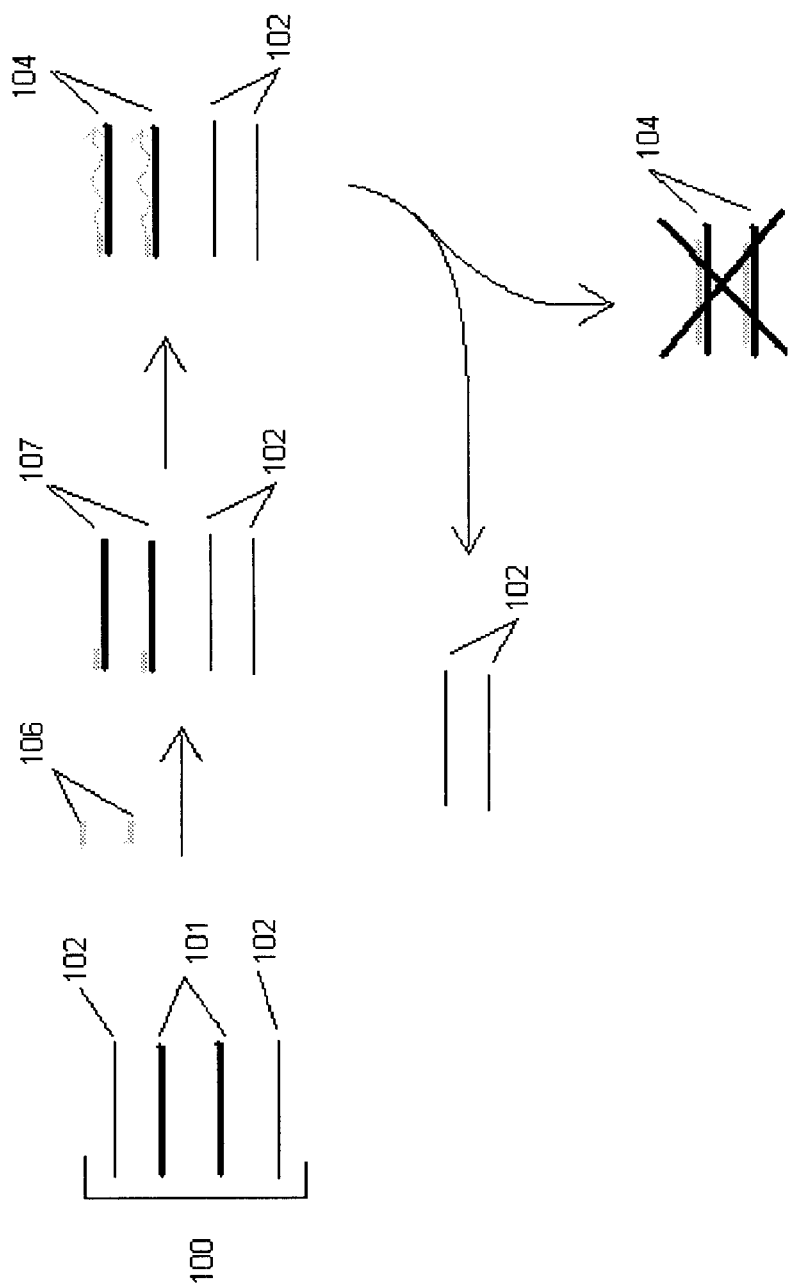
FIG. 3 depicts a schematic illustration of one embodiment of the presently claimed invention wherein bait molecules are synthesized by reverse transcriptase using target molecules as templates.

In a preferred embodiment, rather than adding exogenous DNA as a bait, DNA:RNA hybrids are synthesized "in vivo" using the targeted RNA as a template for reverse transcription. This embodiment is depicted in FIG. 3. Primers 106 which are complementary to the targeted RNA 101 are added to the mixed population 100. The primers are allowed to hybridize to the targeted RNAs forming primer-bound targeted RNAs 107. The primers are extended by reverse transcriptase to form DNA:RNA hybrids 104 which may then be removed using any known method including those methods described below producing an enriched population of interest 102.

Alternatively, a non-nucleic acid bait molecule may be used. For example, an antibody which specifically recognizes and binds the target sequences may be employed in some embodiments of the presently claimed invention. For example, an antibody may be modified to recognize DNA:RNA hybrids or specific rRNA sequences.

The method of removal may exploit some inherent or modified element of the bait. For example, if the bait is distinguishable by size from the sequences in the population of interest, a method of size separation, such as centrifugation, size separation column, or gel electrophoresis could be employed to remove the bait:target complexes.

Alternatively, the bait molecule can be modified with a selectable element, the properties of which may then be exploited in order to remove the bait:target complex from the mixed population. Non-limiting examples of selectable elements include: nucleic acid sequences, ligands, receptors, antibodies, hapten groups, antigens, biotin, streptavidin, enzymes and enzyme inhibitors. Once a bait molecule containing a selectable element is complexed to the target sequence, the bait:target complex is exposed to a reagent capable of binding said selectable element and the reagent-:bait:target complex is removed from the mixed population.

For example, an antibody may be designed which specifically recognizes and binds rRNA sequences. The antibody may be biotinylated before or after exposure to the rRNA sequences. The biotinylated antibody:rRNA complex is then exposed to streptavadin-coated beads. The magnetic beads with the antibody:rRNA complex attached may then be removed from the mixed population.

In some embodiments, the bait molecules may be attached to a solid substrate such as beads, fibers, or an array. The bait molecules may be attached to the solid substrate using any known method including chemical or physical attachment. For example, nucleic acid sequences may be synthesized directly on the solid support (see, e.g., Merrifield, "Solid Phase Peptide Synthesis," J. Am. Chem. Soc., (1963) 85:2149–2154, Fodor et al., "Light Directed Spatially Addressable Parallel Chemical Synthesis" Science (1991) 251:767–773, PCT publication WO90/15070, and U.S. Pat. Nos. 5,800,992, 5,445,934, 5,837,832 and 5,744,305) or pre-synthesized and then attached to the solid support (see e.g. PCT publication No. WO92/10092 and U.S. Pat. Nos. 5,677,195, 5,412,087, 6,022,963 and 6,040,193.)

For those embodiments employing bait molecules attached to solid supports, enzymatic removal of the bound target sequences may be employed if there is a desire to recycle the bait molecules. The method of removing the solution from the solid supports may include any manual or mechanical means including pipetting, or draining in a fluidics station, so long as the solution is obtained in a manner so as to preserve the integrity of the sequences of interest. Otherwise, as indicated above, one may simply remove the solid support containing the bound target sequences, thereby removing the target sequences (and the bait molecules) and enriching for the population of interest.

In practice, the method of removal will vary depending on the type of solid support used. For example, if the solid support is an array, the unbound sequences may simply be washed off the support and the solution collected. If the solid support is a bead, the beads may be removed from solution by centrifugation. If the solid support is a magnetic bead, the beads may be removed from solution by exploiting the magnetic properties of the beads. Regardless of the method used, the solution containing the unbound sequences is isolated from the solid support-bound bait:target complexes.

Figure 4:
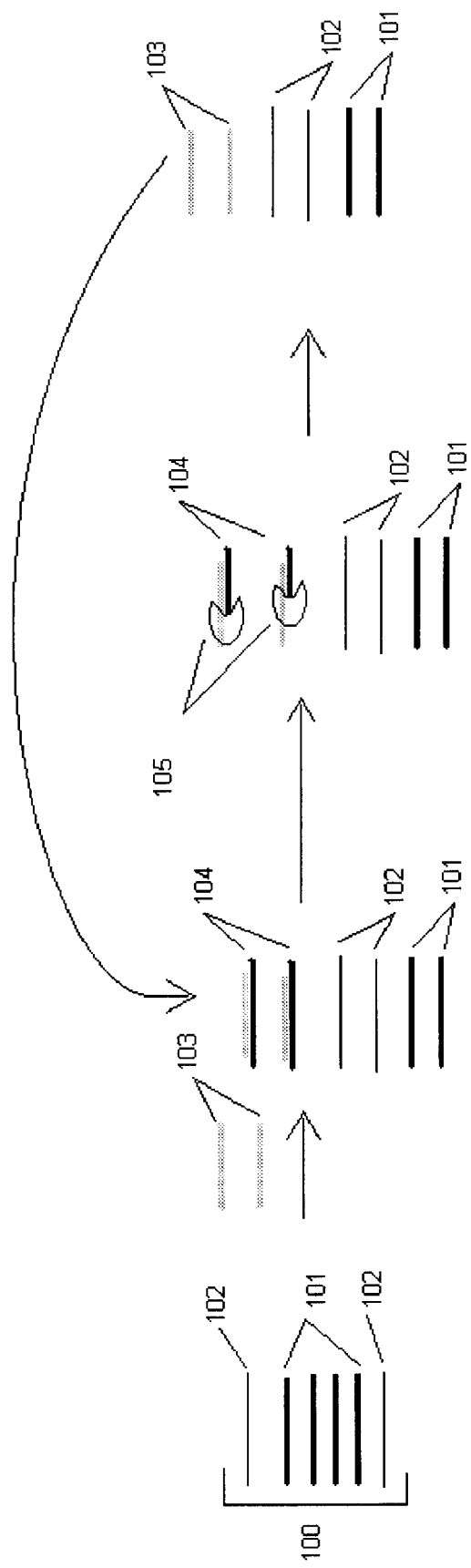
FIG. 4 depicts a schematic illustration of one embodiment of the presently claimed invention in which bait molecules are recycled to initiate repeated rounds of target depletion.

FIG. 4 depicts another embodiment of the presently claimed invention in which the same bait molecule is used for repeated rounds of target depletion. In FIG. 4, a mixed population of nucleic acids 100 includes the population of interest 102 and targeted sequences 101. Bait molecules 103 which are complementary to the targeted sequences but not to the sequences in the population of interest are added to the mixed population under conditions suitable to allow formation of bait:target complexes 104. Next, an enzyme or process 105 specifically targets and removes the target sequence from the bait:target complexes leaving the population of interest 102, DNA bait molecules 103 and any undigested target sequences 101. The remaining DNA bait molecules are then free to hybridize with any undigested target sequences to form new bait:target complexes, thereby repeating the first step. The cycle can then be repeated as desired.

A preferred mechanism for carrying out repeated recycling of DNA bait molecules employs cycling of different conditions. As above, a mixed population of nucleic acids includes a population of interest and target sequences. First, bait molecules are added to the mixed population under conditions suitable to allow formation of bait:target complex. This first step is performed under a first condition, for example at a temperature X. Second, an enzyme or process which specifically targets and removes target sequences which are part of a bait:target complex is added, yielding bait molecules and the population of interest. This second step is performed under a second set of conditions which are different from the conditions required for the first step, i.e. if the first step is performed at temperature X, the second step is performed at temperature Y where Y≠X. Conditions are then returned to those in the first step (i.e. the temperature is returned to X) and the bait molecules are allowed to complex with any target sequences that were not removed in the previous step. The conditions and steps are cycled in this manner until the desired amount of target sequence is removed. In this embodiment, the same bait molecules serve as bait for numerous rounds of target depletion. At the end of the cycling process, the bait molecules may be removed by an enzyme or process which specifically targets and removes the bait. Note, the initial bait molecules may be introduced by reverse transcribing the target sequences as described above and depicted in FIG. 3.

In a particular example of the above embodiment, a mixed population of RNAs includes mRNA, 23S rRNA and 16S rRNA. Cloned ribosomal DNA (rDNA) bait molecules which are complementary to the 23s and 16s rRNAs are added to the mixed population under conditions suitable to allow for the formation of DNA:RNA hybrids. In a preferred embodiment, the rRNA and rDNA annealing reaction is performed at a temperature range of between 37° C. and 95° C., more preferably between 50° C. and 80° C. and more preferably at 70° C. Next, a thermostable RNAse H is added to digest the bound rRNA sequences. In a preferred embodiment this step is performed at a temperature range of between 37° C. and 70° C., more preferably at a temperature range of between 40° C. and 60° C. and more preferably at 50° C. The digestion yields rDNAs, mRNAs and undigested rRNAs. Thereafter, the temperature is raised to a temperature suitable for reannealing, e.g. 70° C., and the annealing step is repeated. Thereafter, the temperature is changed to a temperature suitable for digestion, e.g. 50° C. and the digestion step is repeated. In this manner, the temperature can be cycled to allow for repeated targeting of rRNA molecules by the same DNA bait molecule. It should be noted that it is not necessary to employ different temperatures or conditions to conduct bait cycling as the DNA bait will become available once the RNA target sequence is removed by RNAse H. However, temperature cycling may promote higher specificity and is, therefor, a preferred embodiment for certain applications requiring high specificity.

In a preferred embodiment, once both the targeted RNA and DNA bait molecules have been digested, the RNA of interest is further purified using methods known in the art, including, for example, commercially available purification kits such as the MasterPure complete DNA/RNA purification kit (Epicentre Technologies, WI) or the RNeasy Kit (Qiagen, Valencia, Calif.).

Once the population of interest is enriched, it is often desirable to label the sequences in preparation for a number of different analyses. In one embodiment of the presently claimed invention, the enriched population of interest is fragmented and labeled. In the methods of the presently claimed invention the label is a signal moiety. In a preferred embodiment the label is a biotin and in an even further preferred embodiment the label is a PEO-Iodoacetyl biotin.

Generally under the methods of the presently claimed invention, the fragmented sequences of interest are chemically modified such that the 5' ends comprise a reactive group. The reactive group is then reacted with the signal moiety to produce labeled fragments. In an alternate method, the 5' end modification step is skipped and the fragments are directly labeled with the signal moiety.

Figure 5:
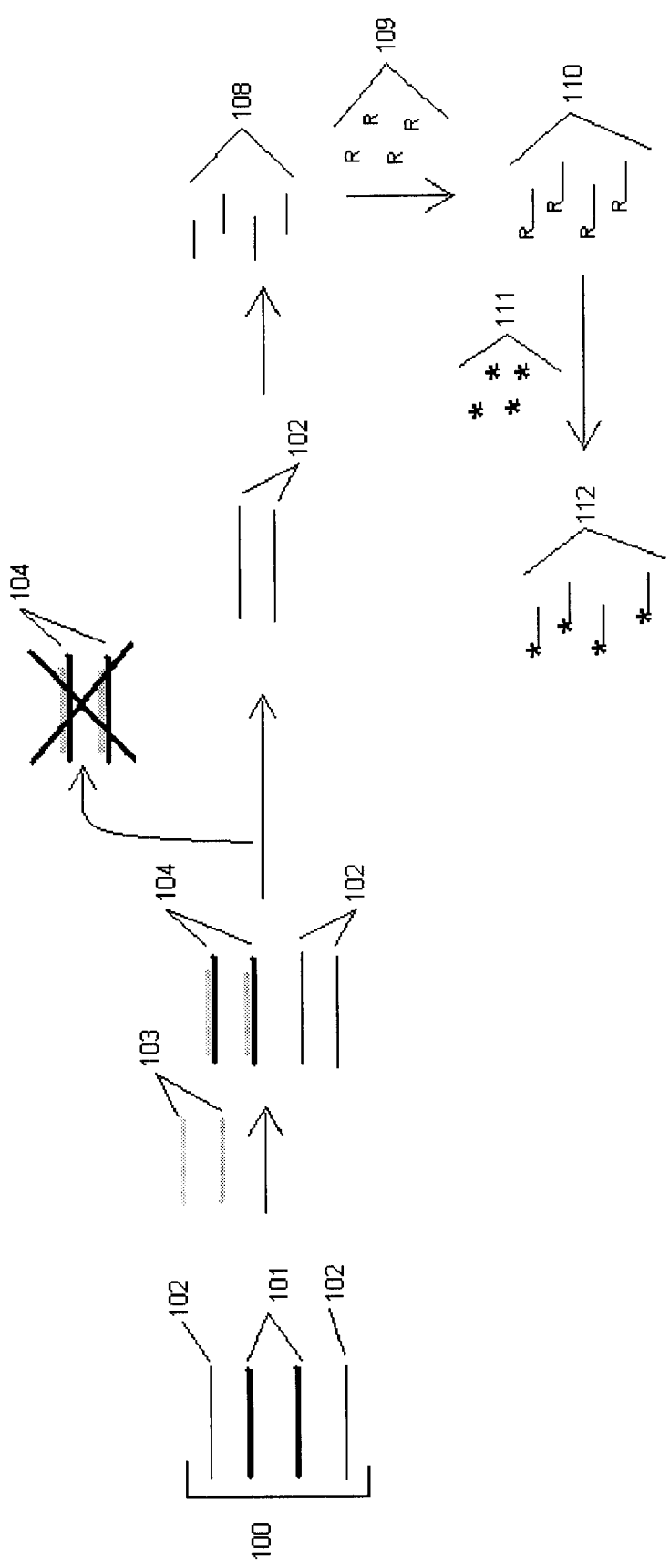
FIG. 5 depicts a schematic illustration of one embodiment of the presently claimed invention in which sequences from an enriched population of interest are labeled.

FIG. 5 depicts a specific example of one embodiment of the presently claimed invention in which enriched fragments are biotin labeled. A mixed population of nucleic acids 100 includes a population of interest 102 and target sequences 101. Bait molecules 103 are added to the mixed population under conditions suitable to formation of bait:target complexes 104. The bait:target complexes are removed leaving an enriched population of interest. If desired, the sequences from the population of interest may be further purified by known purification means (not shown). The sequences from the population of interest are then fragmented producing fragments 108. The fragments are then chemically altered to add a reactive group 109 to the 5' end of each fragment producing reactive fragments 110. Finally, a signal moiety 111 is reacted with the reactive groups to produce labeled fragments 112.

Any known method of fragmentation may be employed. Various methods of fragmenting nucleic acids will be known to those of skill in the art. These methods may be, for example, either chemical or physical in nature. Fragmentation may include partial degradation with a DNAse, RNAse, partial depurination with acid followed by heating, and restriction enzymes or other enzymes which cleave nucleic acid at known or unknown locations. Physical fragmentation methods may involve subjecting the nucleic acid to a high shear rate. High shear rates may be produced, for example, by moving nucleic acid through a chamber or channel with pits or spikes, or forcing the nucleic sample through a restricted size flow passage, e.g. an aperture having a cross sectional dimension in the micron or submicron scale. Particular care must be taken when fragmenting RNA as it is easily degraded. Those of skill in the art will be familiar with methods of fragmenting RNA. In a preferred embodiment, the RNA is fragmented by heat and ion-mediated hydrolysis.

Reactive groups and methods of modifying nucleic acid sequences to contain reactive groups will be well known to those of skill in the art. In a particularly preferred embodiment the nucleic acid fragments are enzymatically modified by T4 polynucleotide kinase and γ-S-ATP to add a 5' thiol group suitable for biotinylation to the 5' end of the nucleic acid fragments thus producing thiolated nucleic acid fragments. See, for example, "Current Protocols in Molecular Biology," Ausubel et al editors, section 3.10.2–3.10.5 (1987) for a discussion of T4 Polynucleotide Kinases.

In one embodiment of the presently claimed invention, a detectable signal moiety is then reacted with the modified or unmodified 5' end of the fragments to produced labeled fragments. In a preferred embodiment, a biotin group such as PEO-Iodoacetyl Biotin, is conjugated to 5'-ends of the fragments which have been modified by T4 polynucleotide kinase and γ-S-ATP. In a particularly preferred embodiment, the label is supplied to the nucleic acid by the addition of oxide biotinyl-iodacetamidyl-3,6-dioxaoctanediamine (Iodoacetyl Biotin) and more preferably by the addition of polyethylene oxide biotinyl-iodacetamidyl-3,6-dioxaoctanediamine (PEO-Iodoacetyl Biotin). PEO-Iodoacetyl Biotin (Pierce Chemical Co. Product #21334ZZ) is a long-chain, water-soluble, sulfhydryl (—SH)-reactive biotinylation reagent. The PEO spacer arm imparts high water solubility. Iodoacetyl Biotin (Pierce Chemical Co. Product #21333ZZ) is generally dissolved in DMSO or DMF before use. The iodoacetyl functional group reacts predominantly with free —SH groups. The reaction occurs by nucleophilic substitution of iodine with a thiol group, resulting in a stable thio-ether bond. The use of PEO-Iodoacetyl Biotin as a biotinylation reagent for proteins and antibodies has been described previously. See, for example, Instructions for EZ-Link™ PEO-Iodoacetyl Biotin, Pierce Chemical Co. We have found that PEO-Iodoacetyl Biotin is also a suitable label for nucleic acids. The use of Iodoacetyl Biotin as a biotinylation reagent for antibodies is described in, for example, U.S. Pat. No. 5,137,804. The use of Iodoacetyl Biotin as a label for the enzyme kinase is described in, for example, Jeong et al. Kinase "Assay Based on Thiophosphorylation and Biotinylation," Biotechniques 27:1232–1238 (December 1999). We have also found that PEO-Iodoacetyl Biotin can be conjugated to a nucleic acid fragment without 5' modification.

Other detectable signal moieties suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label. Colloidal gold label can be detected by measuring scattered light.

After purification of the product, the efficiency of the labeling procedure can be assessed using, for example, a gel-shift assay. In this assay, the addition of biotin residues is monitored by comparing fragments which are pre-incubated with avidin prior to electrophoresis with fragments where no avidin has been added. Biotin-containing residues are retarded or shifted "upwards" on the gel during the electrophoresis due to avidin binding. The nucleic acids are then detected by staining. An absence of a shift pattern is an indication of no or poor biotin labeling.

The above disclosed labeling method may be employed for any nucleic acid molecule including both RNAs and DNAs. Furthermore, the labeling method may be performed without the enrichment protocol.

METHODS OF USE

Array-Based Assays

The nucleic acids isolated and or labeled by the methods described in this disclosure may be analyzed by hybridization to nucleic acid arrays. Those of skill in the art will appreciate that an enormous number of array designs are suitable for the practice of this invention. High density arrays may be used for a variety of applications, including, for example, gene expression analysis, genotyping and variant detection.

Various techniques for large scale polymer synthesis and probe array manufacturing are known. Some examples include the U.S. Pat. Nos.: 5,143,854, 5,242,979, 5,252,743, 5,324,663, 5,384, 261, 5,405,783, 5,412,087, 5,424,186, 5,445,934, 5,451,683, 5,482,867, 5,489,678, 5,491,074, 5,510,270, 5,527,681, 5,550,215, 5,571,639, 5,593,839, 5,599,695, 5,624,711, 5,631,734, 5,677,195, 5,744,101, 5,744,305, 5,753,788, 5,770,456, 5,831,070, 6,040,193 and 5,856,011, all of which are incorporated by reference in their entirety for all purposes.

For gene expression analysis, the high density array will typically include a number of probes that specifically hybridize to the nucleic acid(s) whose expression is to be detected. Array based methods for monitoring gene expression are disclosed and discussed in detail in U.S. Pat. Nos. 5,800,992, 5,871,928, 5,925,525, 6,040,138 and PCT Application WO92/10588 (published on Jun. 25, 1992), all incorporated herein by reference for all purposes. Generally these methods of monitoring gene expression involve (1) providing a pool of target nucleic acids comprising RNA transcript (s) of one or more target gene(s), or nucleic acids derived from the RNA transcript(s); (2) hybridizing the nucleic acid sample to a high density array of probes and (3) detecting the hybridized nucleic acids and calculating a relative expression (transcription, RNA processing or degradation) level.

For genotyping and variant detection, the high density array will typically include a number of probes which are designed to interrogate a particular position which is believed or known to be associated with sequence variation. Array based methods for variant detection are disclosed and discussed in detail in U.S. Pat. Nos. 5,837,832, 5,856,104, 5,856,092, 5,858,659, 6,027,880 and 5,925,525 each of which is incorporated herein by reference for all purposes. Generally these methods of variant detection involve (1) providing a pool of target nucleic acids comprising DNA from the region(s) to be interrogated (2) hybridizing the nucleic acid sample to a high density array of probes and (3) detecting the hybridized nucleic acids and determining the presence or absence of a sequence variant.

Creation of an mRNA library

The methods of the presently claimed invention can be used to create an mRNA library. The present techniques are particularly useful in creating an mRNA library from prokaryotic cells since prokaryotic mRNA lacks the polyA tail that is traditionally used to isolate mRNA populations from complex nucleic acid samples. Briefly, a sample is obtained from an individual. The sample is then enriched for mRNA using the techniques described by the presently claimed invention. Then, following standard protocols known in the art, enriched mRNA can then be used as a template for cDNA synthesis. The cDNA second strand is then synthesized. Adaptors are ligated to the double stranded cDNA and the double stranded cDNA sequences are cloned into appropriate vectors.

Those of skill in the art will be familiar with methods for creating mRNA libraries. See, e.g. Maniatis et al., "Molecular Cloning: A Laboratory Manual, $2^{nd}$ Ed. Cold Spring Harbor Laboratory Press, Cold Spring Harbor N.Y. (1989) ("Maniatis et al.,") especially Chapter 8 which is incorporated by reference in its entirety for all purposes.

CDNA synthesis typically involves the addition of short oligonucleotides which act as primers for reverse transcriptase. These short oligonucleotides may be of a specific known sequence, or may be of random sequence. The length and sequence of the short oligonucleotides will vary based upon the sequence to be reverse transcribed but preferably the short oligonucleotides are between 5 and 10 bases in length and most preferably are about 6 bases in length. Methods of cDNA synthesis are described, for example, in Maniatis et al., see especially sections 8.11–8.13.

For a description of second strand synthesis see, e.g. Maniatis et al., section 8.13–8.17. Methods of ligating adaptors to the double stranded sequences and cloning those sequences into suitable vectors will be known to those of skill in the art and are well described in Maniatis et al., Chapter 8, sections 8.23–8.45. Analysis of cDNA libraries is described throughout Chapter 8 of Maniatis et al.

EXAMPLES 1. mRNA enrichment by removal of 16S and 23S rRNA using in vivo cDNA synthesis The following procedure was performed in PCR tubes in a thermocycler. An initial mixture was prepared by mixing 25 $\mu$g of total *E. coli* RNA to 13.75 $\mu$L of 5.0 $\mu$M rRNA Reverse Transcriptase (RT) Primer Mix, and adding deionized water (DI H$_2$O) to a final volume of 30 $\mu$L and a concentration of 0.83 $\mu$g/$\mu$L of RNA.

The following primers were used to target 16S and 23S RNA (each primer is 5 $\mu$M in the RT primer mix):

16S 1514 5'-CCTACGGTTACCTTGTT-3'
16S889 5'-TTAACCTTGCGGCCGTACTC-3'
16S541 5'-TCGATTAACGCTTGCACCC-3'
23S2878 5'-CCTCACGGTTCATTAGT-3'
23SEco2064 5'-CTATAGTAAAGGTCACGGG-3'
23SEco1159 5'-TCGTCATCACGCCTCAGCCT-3'
23S1012 5'-TCCCACATCGTTTCCCAC-3'
23S539 5'-CCATTATACAAAAGGTAC-3'

The RNA/RT primer mix/DI H$_2$O mixture was heated to 70° C. for 5 minutes and then transferred to 4° C.

To the above mixture, a reverse transcription mixture including 10 $\mu$L of 10× MMLV RT Buffer, 5 $\mu$L of 100 mM DTT, 2 $\mu$L of 25 mM dNTP Mix, 3 $\mu$L of 24.5 U/$\mu$L RNAse Inhibitor (RNAguard Ribonuclease Inhibitor (Porcine), Amersham Pharmacia Biotech, P/N 27-0816-01), 6:L 50 U/$\mu$g MMLV Reverse Transcriptase (Epicentre Technologies, P/N MCR85101) and 44 $\mu$L of DI H$_2$O was added and the reaction was carried out at 42° C. for 25 minutes and transferred to 45° C. for an additional 20 minutes. The mixture was then transferred to 4° C.

The rRNA in the DNA:RNA hybrids was then digested by adding 5 μL of 10 U/μL RNAse H (Epicentre Technologies, P/N R0601K) at 37 C. for 45 minutes. The enzyme was heat deactivated at 65° C. for 5 minutes and then transferred to 4° C.

The DNA was then removed by adding 2.5 μL of 5 U/μl DNAse I (Amersham-Pharmacia Biotech P/N 27-0514-01) and 1 μL of 24.5 U/μL RNAse inhibitor. Digestion was carried out at 37° C. for 20 minutes and the enzyme was deactivated by adding EDTA to a final concentration of 10 mM.

After the reaction was completed, the product was purified (RNeasy Total RNA Isolation Kit, QIAGEN P/N 74104). The sample and another sample of unmodified *E. coli* total RNA were then labeled using the methods described below in Example 4 and separately hybridized to *E. coli* Genome Array (Affymetrix, Inc., Santa Clara, Calif. P/N 510051). The hybridized arrays were then washed, stained and scanned using standard methods as described in the *E. coli* Genome Array User's Manual (Affymetrix, Inc., Santa Clara, Calif.).

Figure 6:
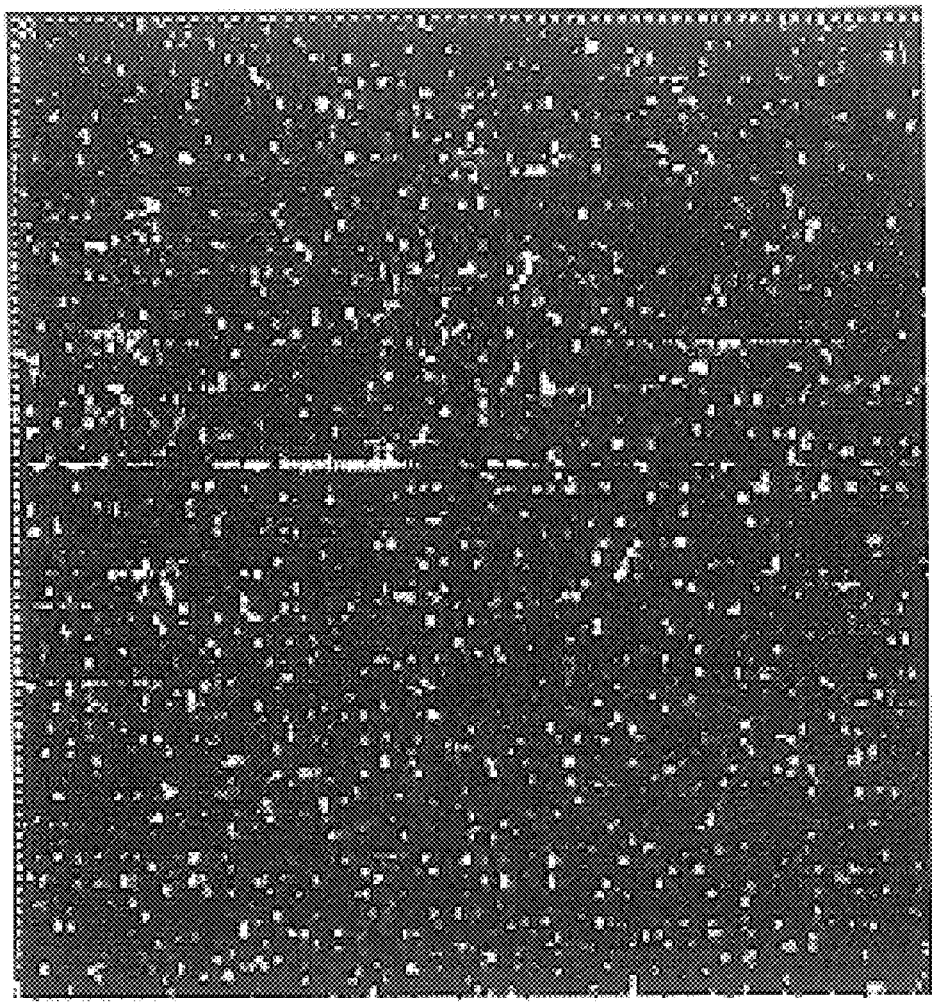
FIG. 6 is an image of unenriched RNA hybridized to a microarray.
Figure 7:
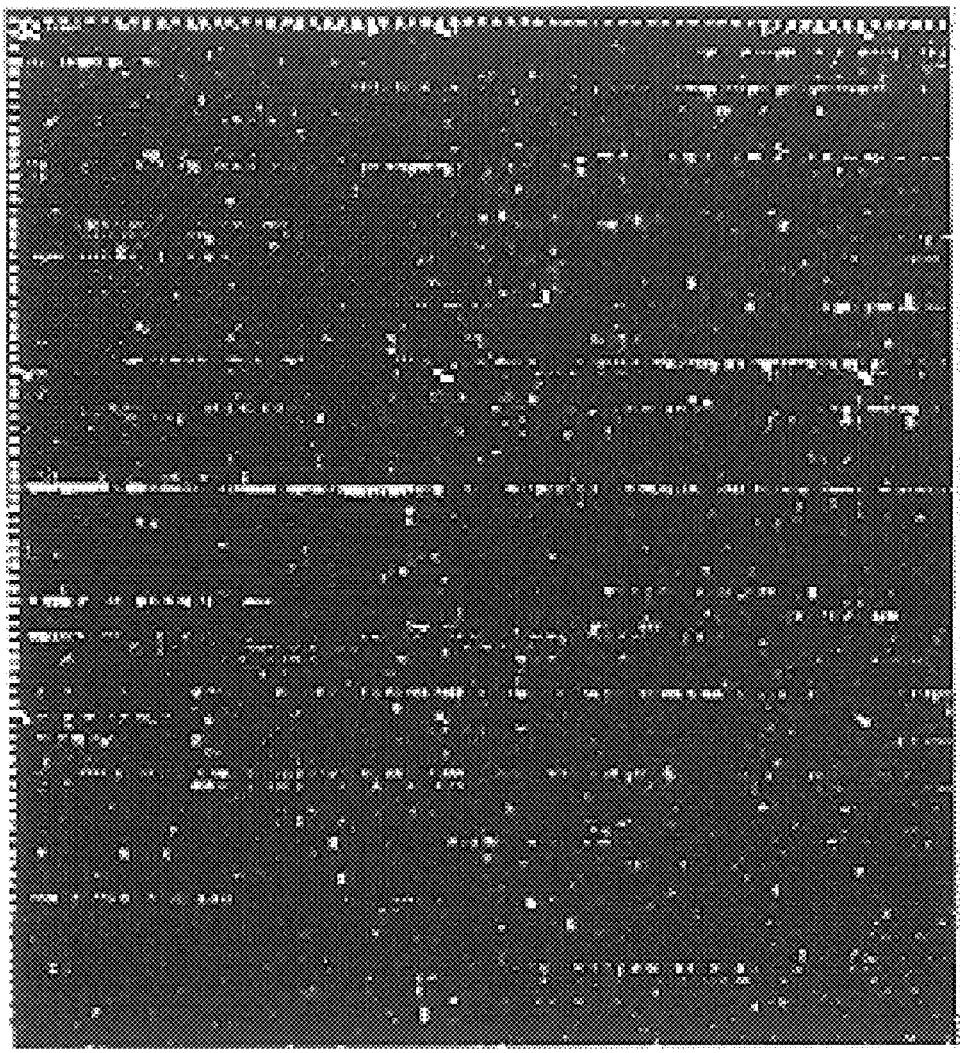
FIG. 7 is an image of enriched RNA hybridized to a microarray.

The removal efficiency for 16s and 23s rRNA is typically between 80–90%. FIGS. 6 and 7 show the results of hybridization of enriched and non-enriched RNA to microarrays. FIG. 6 shows hybridization of labeled unenriched RNA to a microarray. FIG. 7 shows hybridization of labeled enriched RNA to an identical microarray. As can be seen by comparing FIGS. 6 and 7, the hybridization in FIG. 7 shows a much cleaner hybridization with less signal produced by cross hybridization.

2. mRNA enrichment by removal of 16S and 23S rRNA using exogenous DNA

Cloned DNAs encoding the *E. coli* 16S and 23S rRNA genes were amplified separately by PCR and purified with the QIAquick PCR purification kit (QIAGEN P/N 28104). One μg of 16S and 1 μg of 23S rDNA were combined in a PCR tube and diluted to 25 μL with DI $H_2O$. The DNA was denatured by heating at 99° C. for 5 minutes in a thermocycler. The tube was transferred to 70° C. followed by the addition of 25 μL of a prewarmed (at 70° C.) solution containing 1 μg *E. coli* total RNA, 200 mM NaCl, 100 mM Tris (pH 7.5). The tube was incubated at 70° C. for 30 minutes to permit annealing of the rRNAs to the corresponding complementary strand of rDNA (approximately 1:1 molar ratio). The tube was then transferred to 37° C. followed by the addition of 50 μL of a prewarmed (at 37 C.) solution containing 2 units of *E. coli* RNAseH (Epicentre Technologies P/N R0601K), 50 mM Tris (pH 7.5), 100 mM NaCl, 20 mM $MgCl_2$, and the reaction was incubated at 37° C. for 20 minutes to digest RNA from DNA:RNA hybrids. DNA was then digested by the addition of 2 units of DNAse I (Epicentre Technologies, P/N D9902K) and incubation at 37° C. for 15 minutes. EDTA was then added to a final concentration of 20 mM to inhibit further nuclease activity. RNA was purified with an RNeasy column (QIAGEN P/N 74104) and then analyzed in a denaturing agarose gel stained with ethidium bromide.

Figure 8:
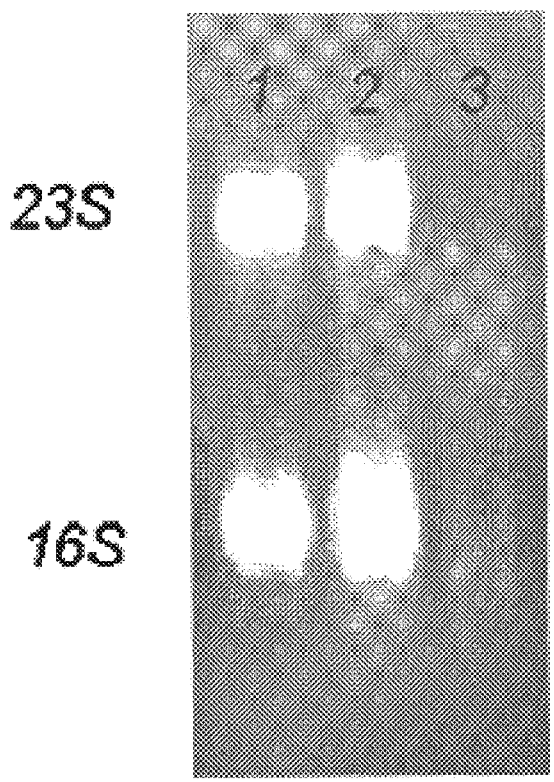
FIG. 8 is a gel image showing the depletion of 23S and 16S RNA using the methods of the presently claimed invention.

FIG. 8 is a gel image of three samples. Lane 1 is an untreated sample. Lane 2 is an enriched sample where the RNAse A step was not performed. Lane 3 is an enriched sample. Comparison of lanes 1, 2, and 3 indicates that the loss of the 16S and 23S rRNA bands in the enrichment procedure resulted from the specificity of RNAse H for DNA:RNA hybrids.

3. mRNA enrichment by removal of 16s and 23s rRNA using DNA bait recycling

Figure 9:
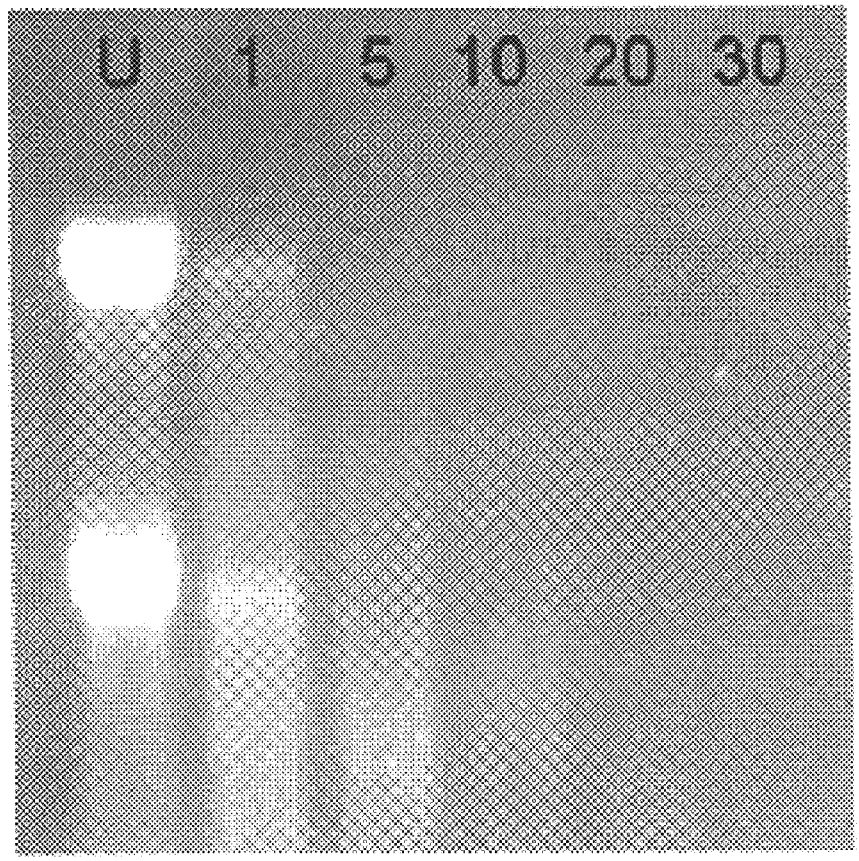
FIG. 9 is a gel image showing the depletion of 23S and 16S RNA using the methods of the presently claimed invention including bait cycling.
Figure 10:
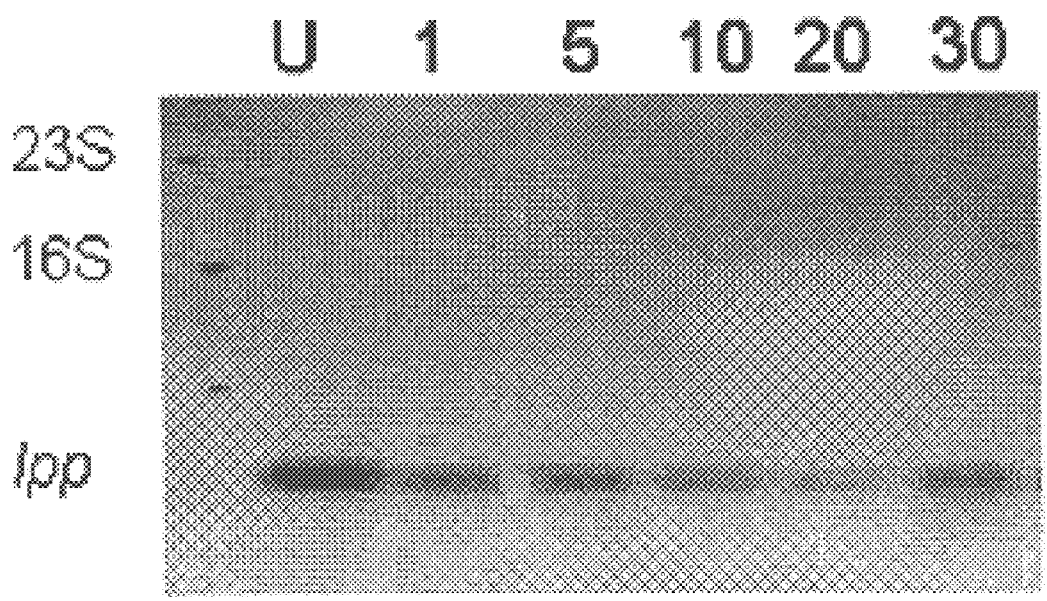
FIG. 10 is an image of a Northern transfer showing the amount of mRNA transcript present during each round of rRNA depletion during a bait cycling experiment.

Cloned DNAs encoding the *E. coli* 16S and 23S rRNA genes were amplified separately by PCR and purified with the QIAquick PCR purification kit (QIAGEN P/N 28104). 0.6 μg of 16S and 0.6 μg of 23S rDNA were combined in a PCR tube and diluted to 48 μL with DI $H_2O$. The DNA was denatured by heating at 99° C. for 5 minutes in a thermocycler. The temperature was lowered to 70° C. followed by the addition of 48 μL of a prewarmed (at 70° C.) solution containing 6 μg *E. coli* total RNA, 200 mM NaCl, 100 mM Tris (pH 7.5), and 12 units of thermostable RNAse H (Epicentre Technologies, P/N H39100). The tube was incubated at 70° C. for 1 minute to permit annealing of the rRNAs to the corresponding complementary strand of rDNA (approximately 1 mole DNA per 10 moles RNA). The temperature was reduced to 50° C. for 5 minutes to complete one cycle of enrichment. The temperature was then increased to 70° C. for 1 minute then again reduced to 50° C. for 5 minutes to complete the second cycle. This temperature cycling was repeated a total of 30 times. After 1, 5, 10, 20, and 30 cycles 16 μL (corresponding to 1 :g RNA from the starting mixture) was removed from the tube and mixed with 1 unit DNAse I (Epicentre Technologies, P/N D9902K) and incubated at 37° C. for 15 minutes. EDTA was then added to a final concentration of 20 mM to inhibit further nuclease activity. RNA was purified from each sample with an RNeasy column (QIAGEN P/N 74104) and then analyzed in a denaturing agarose gel, along with 1 μg of untreated *E. coli* total RNA (FIG. 9). The diminishing amounts of 23S and 16S RNA as cycles are repeated can be seen by comparing the lanes from left to right. The first lane (labeled U) is untreated. The next lanes are the amount of 23S and 16S RNA after 1, 5, 10, 20 and 30 cycles, respectively.

The gel was transferred to a nylon membrane (Northern transfer) and the quantity of a particular mRNA transcript, from the *E. coli* lpp gene, was deduced by hybridization to a digoxigenin-labeled lpp probe (Roche P/N 1636090), followed by detection with anti-DIG-alkaline phosphatase and NBT/BCIP (Roche P/N 1175041) (10). It is apparent that the bands corresponding to the 23S and 16S rRNAs are reduced much more with successive cycles than the band corresponding to the lpp transcript, an indication of specific reduction of rRNA and relative enrichment of mRNA. The enrichment demonstrates that the input exogenous DNA bait is "recycled," that is, each complementary rDNA molecule can direct the destruction of multiple rRNA molecules.

4. mRNA labeling (Thiol Kinase—Dependent Method)

Fragmentation and labeling reactions were done in PCR tubes in a thermocycler. A maximum of 20 μg of RNA was used for the fragmentation step. To avoid incomplete fragmentation, multiple tubes were used if the yield of RNA from the enrichment step was greater than 20 μg. The fragmentation reaction mixture comprised 10 μl of 10× NEBuffer for T4 Polynucleotide Kinase (New England Biolabs, P/N 201L), up to 20 μg of RNA and deionized water (DI $H_2O$) up to 88 μl total volume. The reaction was incubated at 95° C. for 30 minutes and then cooled to 4° C.

The 5'-thiolation reaction mixture comprised, 88 μl fragmented RNA, 2.0 μl 5 mM γ-S-ATP (Roche P/N 1162306) and 10 μl of 10 U/μl T4 Polynucleotide Kinase Kinase (New England Biolabs, P/N 201L). The reaction was incubated at 37° C. for 50 minutes and then inactivated at 65° C. for 10 minutes and finally cooled to 4° C.

Excess γ-S-ATP was removed by ethanol precipitation: the samples were removed from the PCR tube(s) and combined in a sterile microcentrifuge tube. ¹/₁₀ volume of 3 M sodium acetate, pH 5.2 (Sigma Chemical, P/N S 7899) and 2.5 volumes of ethanol were added and left on ice for 15 minutes. The tubes were then spun at 14,000 rpm at 4° C. for 30 minutes to pellet the RNA. The pellet was then resuspended in 90 µl of DI H$_2$O.

The RNA was then labeled with biotin. 6.0 µl of 500 mM MOPS, pH 7.5 (Sigma Chemical P/N M3183) was added to 90 µl of fragmented thiolated RNA with 4.0 µl of 50 mM Polyethylene Oxide (PEO)-Iodoacetyl-Biotin (Pierce Chemical, P/N 21334ZZ). The reaction was incubated at 37° C. for one hour and then cooled to 4° C. Unincorporated label was removed using the QIAGEN RNA/DNA Mini Column Kit (QIAGEN P/N 14123). Optionally, for increased RNA recovery, one RNA/DNA column and 5.4 mL Buffer QRV2 per 10.0 µg RNA was used. Additionally, 50 µg of glycogen (Boehringer Mannheim, P/N 901393) per tube was optionally used to act as a carrier and aid in the visualization of the pellet.

The pellet was then dissolved in 20 to 30 µL of Molecular Biology Grade water.

The enriched mRNA preparation was quantified by 260 nm absorbance. Typical yields for the procedure were 2 to 4 µg of RNA. The labeled RNA was stored at −20° C. until ready for use.

The efficiency of the labeling was assessed using a gel shift assay. In this assay, the addition of biotin residues is monitored by comparing fragments which are pre-incubated with avidin prior to electrophoresis with fragments where no avidin has been added. Biotin-containing residues are retarded or shifted "upwards" on the gel during the electrophoresis due to avidin binding. The nucleic acids are then detected by staining. An absence of a shift pattern is an indication of no or poor biotin labeling.

A NeutrAvidin solution of 2 mg/mL or higher was prepared (Pierce Chemical, P/N 31000ZZ). 50 mM Tris, pH 7.0 (Ambion, P/N 9850G) is used to dilute the NeutrAvidin solution. A TBE gel (4%–20%) (Invitrogen, P/N EC62252) was placed into a gel holder and load system with 1× TBE Buffer. For each sample tested, two 150 to 200 ng aliquots of fragmented and biotinylated sample were removed. 5 µl of 2 mg/mL NetrAvidin were added to each tube tested. The mixture was allowed to sit at room temperature for 5 minutes. Loading dye (Amresco, P/N E-274) was added to a 1× dye concentration. 10 bp and 100 bp DNA ladders (Gibco BRL P/N 10821-015 and 15628-019) were prepared and both samples and ladders were loaded on the gel. The gel was run at 150 volts for approximately 1 hour. While the gel was running, SYBR Green I or Gold (Molecular Probes P/N S-7563 or S-1 1494) was prepared for staining. After completion of the gel run, the gel was stained for 10 minutes.

Figure 11:
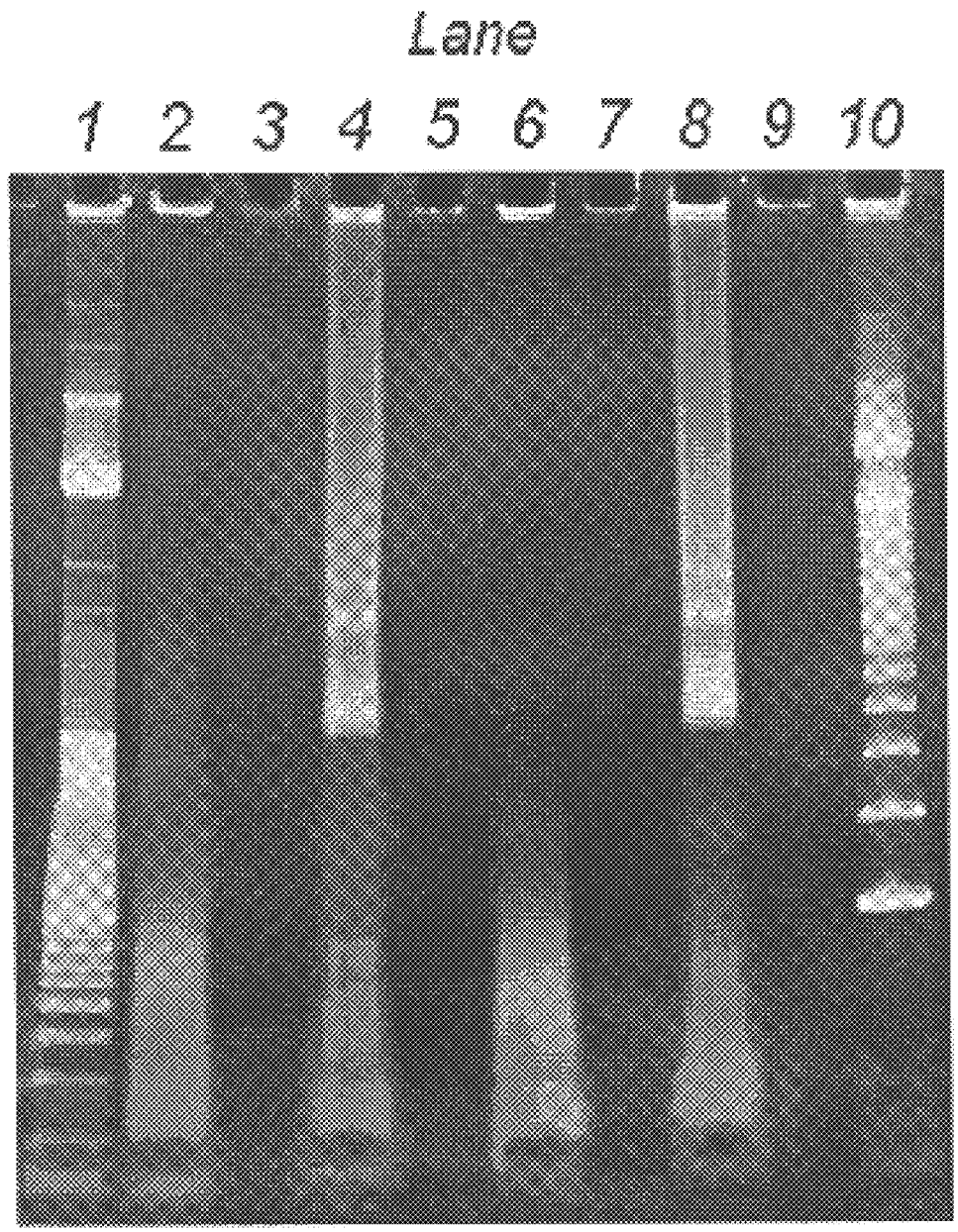
FIG. 11 is a gel image of biotin labeled mRNA fragments.

After staining, the gel was placed in a UV light box to produce an image. FIG. 11 is a gel image of the labeled *E. coli* fragments. Lane 1 is the 10 bp DNA ladder, lane 2 is fragmented and labeled total *E. coli* RNA, lane 3 is fragmented and labeled total *E. coli* RNA with avidin, lane 4 is fragmented and labeled enriched *E. coli* mRNA, lane 5 is fragmented and labeled enriched *E. coli* mRNA with avidin and lane 6 is 100 bp DNA ladder. Lanes 3 and 5 show a clear upward shift as compared to lanes 2 and 4 respectively, thus indicating successful biotin labeling of the RNA fragments.

5. mRNA Labeling (Thiol Kinase—Independent Method)

MRNA enrichment was performed as described Example 1 above. To label the enriched RNA directly with biotin with the thiol kinase (tk)—independent method, the following were combined in a final volume of 100 µL: 10 µg of RNA, 30 mM MOPS, pH 7.5, 20 mM iodoacetyl-PEO-biotin (Pierce Chemicals), 10 mM magnesium chloride. The components were placed in a PCR tube, heated to 95° C. for 30 min, then 25° C. for 30 min and cooled to 4° C. in a PCR instrument as above. Unreactive label was removed from the labeled RNA fragments on RNA/DNA mini-columns (Qiagen). The labeled RNA solution was mixed with 5.4 mL of QRV2 buffer (Qiagen) before loading on a single column. Labeled RNA fragments were precipitated after the addition of 25 µg of carrier glycogen.

Figure 12:
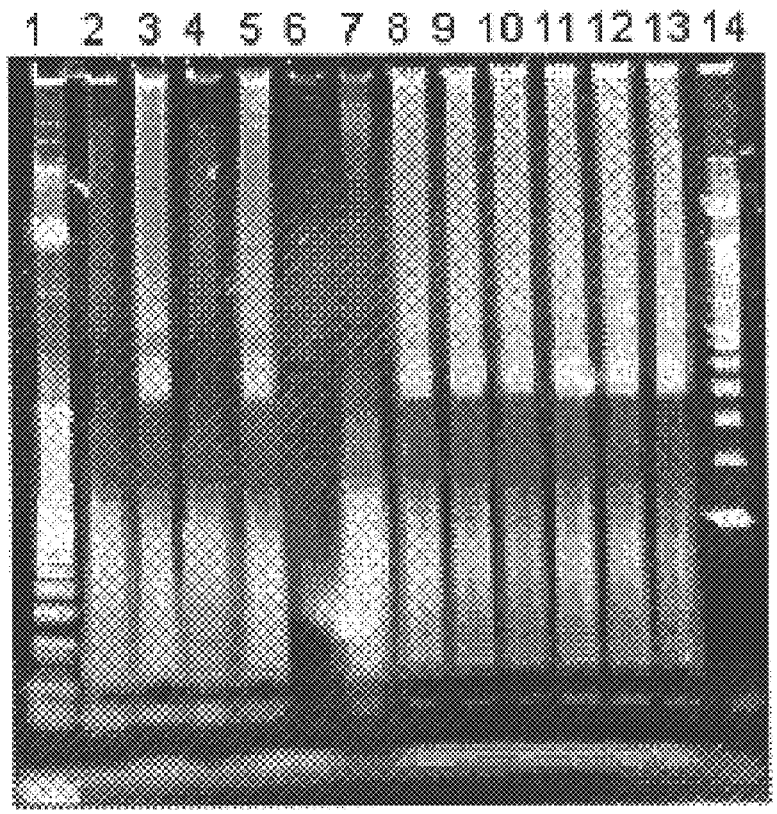
FIG. 12 is a gel image of a gel shift assay.

To compare the efficiency of labeling, gel shift assays were performed as described in example 4 above. FIG. 12 is the gel image. Lane 1 contains a 10 bp DNA ladder, lane 2 contains RNA labeled by the tk-independent method without avidin, lane 3 contains RNA labeled by the tk- independent method with avidin, lane 4 contains RNA labeled by the tk-independent method without avidin, lane 5 contains RNA labeled by the tk-independent method with avidin, lane 6 contains avidin alone as a control, lane 7 contains RNA labeled by the tk-dependent method without avidin, and lanes 8–13 contain RNA labeled with the tk-dependent method with avidin. Lanes 3, 5 and 8–13 all show a clear shift as compared to their respective controls clearly indicating that the RNA fragments have been labeled. Comparison by eye demonstrates that the tk-independent method labels with less intensity than the tk-dependent method. A lower labeling efficiency may be advantageous in samples for which the signal is very strong and data accuracy is inhibited by saturation of the signal.

6. Comparison of *E. coli* Expression Using Both the TK-Dependent and TK-Independent Labeling Methods.

To further compare the two labeling methods, the expression patterns of RNA from *E. coli* strains grown in minimal media and enriched media were analyzed. Cells were grown in either minimal media or enriched media conditions, RNA was isolated from each population, and the RNA was then labeled using either the tk-dependent or tk-independent method. Expression data was analyzed by hybridizing the labeled RNA to microarrays designed to interrogate *E. coli*. The microarray data was then compared to traditional Northern blot and Slot blot data from similarly treated populations of cells.

*E. coli* strain MG 1655 was obtained from the *E. coli* Genetic Stock Center located in Yale University. Luria Broth (Teknova) was used for the enriched medium. Cells were grown at 37° C. on a gyrotory shaker set at 270–280 rpm. Cells were harvested at mid-log phase (OD 0.8–0.9 at 420 nm). Total RNA was isolated using the MasterPure™ RNA Purification Kit (Epicentre).

RNA spike controls were prepared by in vitro transcription of linearized plasmid templates. After purification, the RNA was quantified by its absorbance at 260 nm. Control RNA spikes (2 femtomoles each) were added to the *E. coli* RNA prior to labeling.

The RNA was labeled using the tk-dependent and tk-independent methods described in Examples 4 and 5, respectively. In both cases unreactive label was removed from the labeled RNA fragments on RNA/DNA mini-columns (Qiagen). The labeled RNA solution was mixed with 5.4 mL of QRV2 buffer (Qiagen) before loading on a single column. Labeled RNA fragments are precipitated after the addition of 25 µg of carrier glycogen.

Both samples were then hybridized to *E. coli* Genome Array (Affymetrix, Inc., Santa Clara, Calif. P/N 510051). The hybridized arrays were then washed, stained and scanned using standard methods as described in the *E. coli* Genome Array User's Manual (Affymetrix, Inc., Santa Clara, Calif.).

Figure 13:
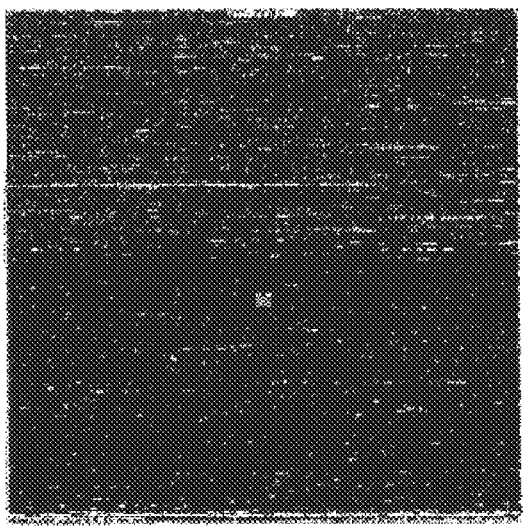
FIG. 13 depicts hybridization patterns of *E. coli* RNA labeled with the thiol-kinase dependent (panel A) and thiol-kinase independent (panel B) methods.
Figure 13:
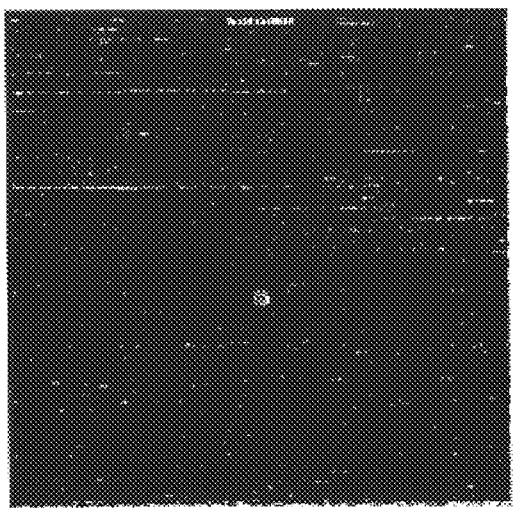

Duplicate assays were run for each method. FIG. 13 is an array image from the experiment. Panel A is the array image of the hybridized *E. coli* RNA labeled with the tk-dependent method. Panel B is an array image of the hybridized *E. coli*

RNA labeled with the tk-independent method. Signal shows up as a bright spot against a dark background. A comparison of the two images by eye shows that the tk-independent method showed a lower level of signal intensity.

Data was analyzed using the GeneChip® Software from Affymetrix, Inc. Calls, Average Difference values and Fold Changes were calculated with GeneChip® Software through the Expression Analysis Window. Default settings were used for the analysis. The number of sequences called present and the median average difference was calculated for each of the labeling techniques and the results are show in Table 1, below.

TABLE 1

|  | Calls in the RNA coding region | | | |
| --- | --- | --- | --- | --- |
|  | thiol kinase method | | non thiol kinase method | |
|  | Exp. A | Exp. B | Exp. 1 | Exp. 2 |
| Total | 4216 | 4216 | 4216 | 4216 |
| #'s Present | 1938 | 2011 | 1928 | 1777 |
| #'s Absent | 2188 | 2130 | 2242 | 2378 |
| % Absent | 51.9 | 50.5 | 53.2 | 56.4 |
| Avg Med Int | 2111 | 1806 | 926 | 815 |

As seen in Table I, row 1 (labeled "Total") a total of 4,216 probe sets representing open reading frames were analyzed. In simplified terms, if a hybridization signal above a certain threshold is detected, the probe set is called present. Row 2 (labeled "#'s Present") shows the number of probe sets representing open reading frames on the array that were called present. If the hybridization signal is below the threshold, the gene is called absent. Row 3 (labeled "#'s Absent") shows the number of genes called absent. For the purposes of this application, "Average Median Intensity" (row 4) is used to quantitate signal intensity readings across the entire array.

Higher signal intensity is observed for the tk-dependent method (row 4, experiments A and B) than with the tk-independent method (row 4, experiments 1 and 2). Comparison of the results in row 4 shows that the tk-dependent method exhibits about half the intensity as the tk-dependent method. Importantly, the decreased signal intensity does not translate into a significant loss in the number of genes called present in the two methods (compare row 2, experiments A and B with row 2, experiments 1 and 2). This result indicates that the tk-independent method labels at about half the intensity of the tk-dependent method. Under some conditions, lower signal intensity may be desirable to prevent loss of accuracy due to signal saturation.

Correlation graphs were prepared using average difference values for all 4,216 probe sets representing open reading frames. For the purposes of this application, average difference is used to demonstrate the signal intensity between probe pairs on the same array. Both techniques create reproducible results as seen in the intra-assay correlation graphs (FIGS. 14 and 15).

Figure 14:
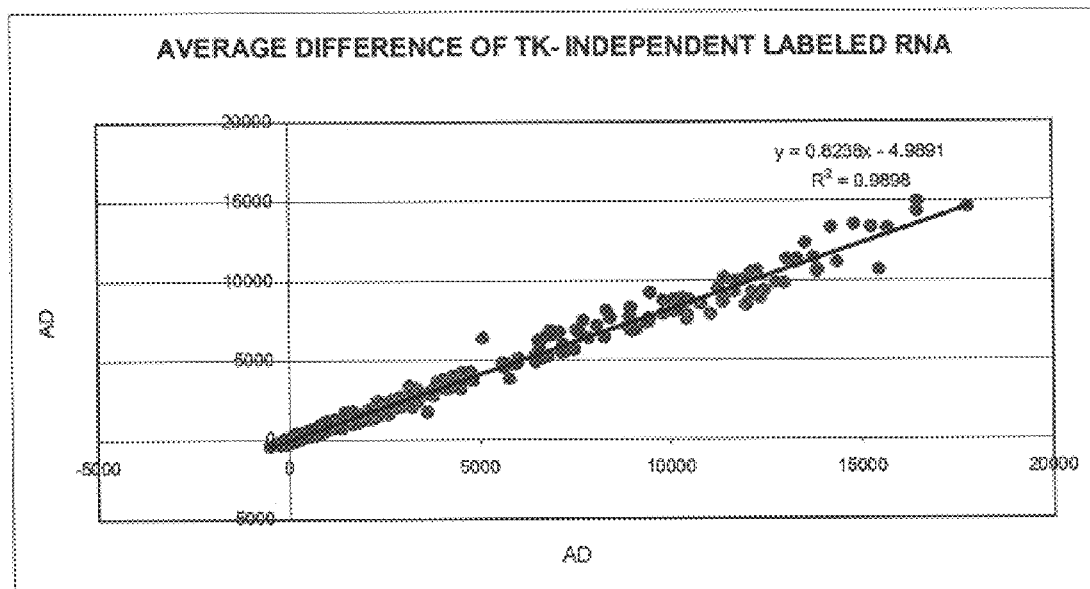
FIG. 14 shows the average difference correlation comparing the results of two different thiol-kinase dependent experiments to each other.

FIG. 14 shows the average difference correlation comparing the results of two different tk-independent experiments to each other. The X axis indicates the average difference results from experiment A and the Y axis indicates the average difference results from experiment B. A perfect correlation, i.e. perfect reproducibility between different experiments would be indicated by an $r^2$ value of 1. The $r^2$ value in this case is 0.991 indicating a good correlation, or in other words, a high degree of reproducibility in signal intensity for the tk-dependent method.

Figure 15:
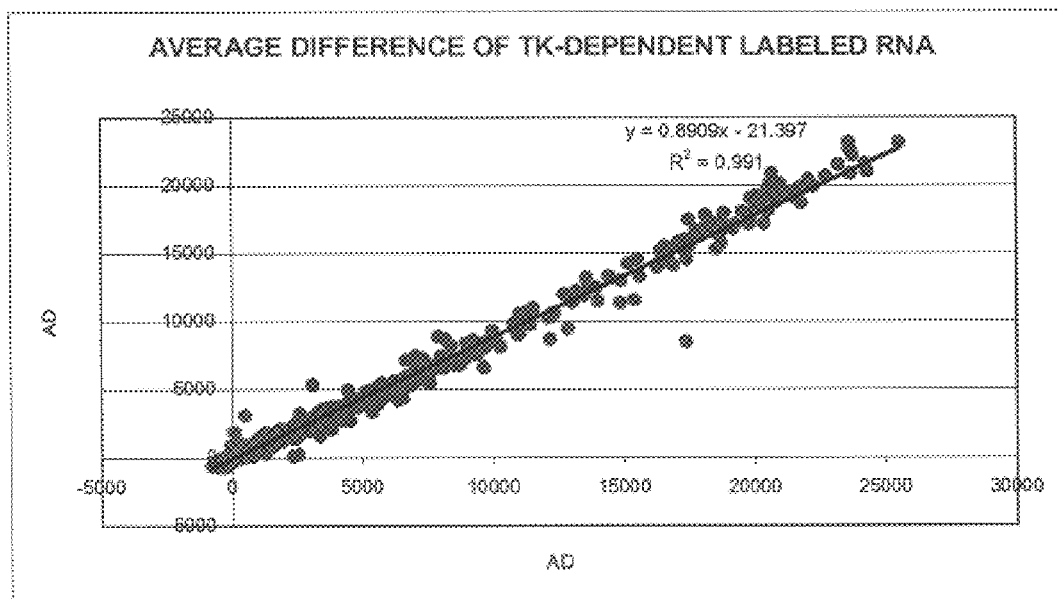
FIG. 15 shows the average difference correlation comparing the results of two different thiol-kinase independent experiments to each other.

FIG. 15 shows the average difference correlation comparing the results of two different tk-dependent experiments to each other. The X axis indicates the average difference results from experiment 1 and the Y axis indicates the average difference results from experiment 2. Again, a perfect correlation would be indicated by an $r^2$ value of 1. The $r^2$ value in this case is 0.9898 indicating a good correlation, or in other words, a high degree of reproducibility in signal intensity for the tk-independent method.

Figure 16:
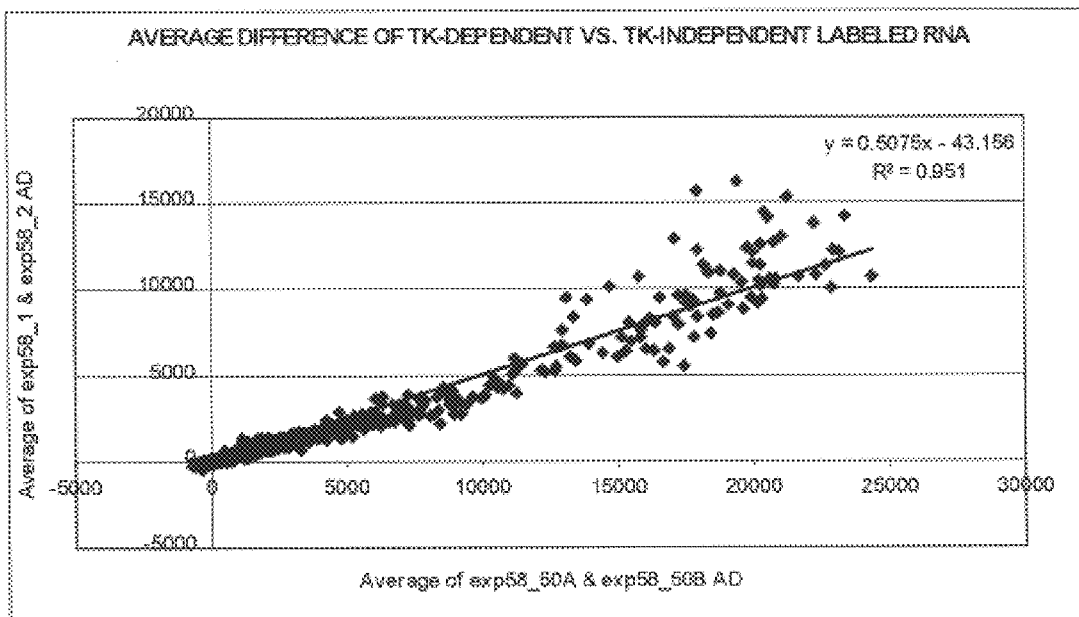
FIG. 16 shows the average difference correlation comparing the thiol-kinase dependent experiments with the thiol-kinase independent experiments.

The two different methods are correlated as seen in FIG. 16. In FIG. 16, the X axis represents the tk-dependent experiments (average of exp. A+exp. B) and the Y axis represents the tk-independent experiments (average of exp. 1+exp. 2). The slope is 0.5075, again indicating that the label in the tk-independent method is about half as intense as the tk-dependent method. Note that the correlation coefficient is 0.951 indicating a high degree of correlation between the two techniques. The major discrepancies are seen at the high intensity levels where the tk-dependent method may have reached saturation.

CONCLUSION

The presently claimed invention provides greatly improved methods for enriching and labeling nucleic acids. It is to be understood that the above description is intended to be illustrative and not restrictive. Many variations of the invention will be apparent to those of skill in the art upon reviewing the above description. By way of example, the invention has been described primarily with reference to the enrichment and labeling of mRNA, but it will be readily recognized by those of skill in the art that the invention may be employed to enrich and label all types of nucleic acids including other forms of naturally and non-naturally occurring polynucleotides such as RNAs and DNAs. Furthermore, it will be understood by those of skill in the art that the enriched and/or labeled nucleotides of the presently claimed invention may be utilized in a wide variety of biological analyses in no way limited to those methods disclosed in the present invention. Therefore, it is to be understood that the scope of the invention is not to be limited except as otherwise set forth in the claims.

What is claimed is:

1. A method of preparing labeled fragments of a population of nucleic acids of interest comprising:

increasing the relative percentage of said population of nucleic acids of interest within a mixed population of nucleic acids, wherein said mixed population comprises a plurality of nucleic acid sequences, comprising:

(a) contacting a nucleic acid sample with a nucleic acid bait molecule, wherein said nucleic acid sample comprises said nucleic acids of interest and at least one unwanted target sequence and wherein said bait molecule binds specifically to said unwanted target sequence, but not to said nucleic acids of interest, under such conditions as to allow for the formation of a bait:target complex;

(b) digesting the unwanted target sequence in the bait:target complex thereby resulting in an increase in the relative percentage of said nucleic acids of interest within said mixed population of nucleic acids;

fragmenting said nucleic acids of interest to produce fragments; and adding a label to the fragments.

2. The method of claim 1 wherein the nucleic acid sample is an RNA sample.

3. The method of claim 1 wherein the nucleic acid sample is derived from a prokaryotic organism.

4. The method of claim 1 wherein the nucleic acid sample is derived from a gram negative prokaryotic organism.

5. The method of claim 1 wherein the nucleic acid sample is derived from *E. coli*.

6. The method of claim 1 wherein said nucleic acids of interest are messenger RNA (mRNA).

7. The method of claim 1 wherein said unwanted target sequence is rRNA or tRNA.

8. The method of claim 1 wherein said target sequence is ribosomal RNA (rRNA).

9. The method of claim 1 wherein said unwanted target sequence is 23S RNA.

10. The method of claim 1 wherein said unwanted target sequence is 16S RNA.

11. The method of claim 1 wherein said bait molecule is generated from a population of nucleic acids other than the nucleic acid of interest.

12. The method of claim 1 wherein said bait molecule is chemically synthesized.

13. The method of claim 1 wherein said bait molecule is cloned from single stranded phage DNA.

14. The method of claim 1 wherein said bait molecule is synthesized by hybridizing a primer to said unwanted RNA target sequence and extending said primer by reverse transcriptase using said target sequence as a template.

15. The method of claim 1 wherein the nucleic acid sample is an RNA sample, the bait molecule is DNA, and the bait:target complex is a DNA:RNA hybrid.

16. The method of claim 14 wherein said bait molecules are synthesized by reverse transcriptase after the addition of at least one primer complementary to 16S RNA and at least one primer complementary to 23S RNA.

17. The method of claim 1 wherein said bait molecule is attached to a solid substrate.

18. The method of claim 17 wherein said solid substrate is a bead.

19. The method of claim 1 wherein said bait molecule is modified to comprise a selectable element.

20. The method of claim 19 wherein said selectable element is selected from the group consisting of: a nucleic acid sequence, a ligand, a receptor, an antibody, a haptenic group, an antigen, an enzyme or an enzyme inhibitor.

21. The method of claim 19 further comprising the step of exposing said bait:target complex to a reagent that binds said selectable element to form a reagent:bait:target complex prior to the step of digesting the unwanted target sequence.

22. The method of claim 21 wherein the reagent that binds said selectable element is selected from the group consisting of: a nucleic acid sequence, a ligand, a receptor, an antibody, a haptenic group, an antigen, an enzyme or an enzyme inhibitor.

23. The method of claim 19 wherein said selectable element is a biotin.

24. The method of claim 21 wherein said selectable element is biotin and said reagent that binds said selectable element is streptavidin.

25. The method of claim 21 further comprising separating said reagent:bait:target complex from said mixed population prior to the step of digesting the unwanted target sequence.

26. The method of claim 25 wherein the reagent:bait:target complex is attached to a solid support.

27. The method of claim 15 wherein the step of digesting said unwanted target sequence comprises exposing said DNA:RNA hybrid to a reagent which digests RNA in a DNA:RNA hybrid and digesting said unwanted target sequence and wherein said reagent is RNAse H.

28. The method of claim 1 further comprising the step of removing the bait molecule after digesting the target sequence in said bait:target complex.

29. The method of claim 27 further comprising the step of removing any remaining DNA bait molecules after said unwanted target sequence is removed.

30. The method of claim 29 wherein said step of removing said DNA bait molecules is accomplished by digestion with DNAse I.

31. The method of claim 28 wherein steps (a) and (b) are repeated.

32. The method of claim 31 wherein the same bait molecule is used to remove multiple target sequences.

33. The method of 32 wherein a thermostable RNAse H is used to remove said target sequences from said bait:target complex.

34. The method of claim 31 wherein step (a) is performed at a first temperature and step (b) is performed at a second temperature.

35. The method of claim 1 wherein said label is a biotin.

36. The method of claim 1 wherein said label is a polyethylene oxide-Iodoacetyl Biotin.

37. The method of claim 1 wherein the label is attached to the 5' ends of said fragments.

38. The method of claim 1 wherein after said step of fragmenting, said 5' ends of said fragments are chemically modified.

39. The method of claim 38 wherein the 5' ends of said fragments are chemically modified by γ-S-ATP and T4 kinase.

40. The method of claim 38 wherein said chemical modification results in the addition of a thiol group to the 5' end of said fragments.

41. The method of claim 40 wherein said detectable signal moiety is polyethylene oxide-Iodoacetyl Biotin.

* * * * *

SEQUENCE LISTING

<160> NUMBER OF SEQ ID NOS: 8

<210> SEQ ID NO 1
<211> LENGTH: 17
<212> TYPE: DNA
<213> ORGANISM: Escherichia coli

```
<400> SEQUENCE: 1
cctacggtta ccttgtt                                                  17

<210> SEQ ID NO 2
<211> LENGTH: 20
<212> TYPE: DNA
<213> ORGANISM: Escherichia coli

<400> SEQUENCE: 2
ttaaccttgc ggccgtactc                                               20

<210> SEQ ID NO 3
<211> LENGTH: 19
<212> TYPE: DNA
<213> ORGANISM: Escherichia coli

<400> SEQUENCE: 3
tcgattaacg cttgcaccc                                                19

<210> SEQ ID NO 4
<211> LENGTH: 17
<212> TYPE: DNA
<213> ORGANISM: Escherichia coli

<400> SEQUENCE: 4
cctcacggtt cattagt                                                  17

<210> SEQ ID NO 5
<211> LENGTH: 18
<212> TYPE: DNA
<213> ORGANISM: Escherichia coli

<400> SEQUENCE: 5
ccattataca aaaggtac                                                 18

<210> SEQ ID NO 6
<211> LENGTH: 20
<212> TYPE: DNA
<213> ORGANISM: Escherichia coli

<400> SEQUENCE: 6
ctatagtaaa ggttcacggg                                               20

<210> SEQ ID NO 7
<211> LENGTH: 20
<212> TYPE: DNA
<213> ORGANISM: Escherichia coli

<400> SEQUENCE: 7
tcgtcatcac gcctcagcct                                               20

<210> SEQ ID NO 8
<211> LENGTH: 18
<212> TYPE: DNA
<213> ORGANISM: Escherichia coli

<400> SEQUENCE: 8
tcccacatcg tttcccac                                                 18
```